(12) United States Patent
DeBeer et al.

(10) Patent No.: US 10,278,804 B2
(45) Date of Patent: May 7, 2019

(54) IVC FILTER RETRIEVAL SYSTEMS WITH RELEASABLE CAPTURE FEATURE

(71) Applicant: AVANTEC VASCULAR CORPORATION, Sunnyvale, CA (US)

(72) Inventors: Nicholas DeBeer, Sunnyvale, CA (US); Frank Becking, Sunnyvale, CA (US); Karl Halden, Sunnyvale, CA (US); Teresa Ruvalcaba, Sunnyvale, CA (US)

(73) Assignee: AVANTEC VASCULAR CORPORATION, Sunnyvale, CA (US)

( * ) Notice: Subject to any disclaimer, the term of this patent is extended or adjusted under 35 U.S.C. 154(b) by 460 days.

(21) Appl. No.: 14/569,567

(22) Filed: Dec. 12, 2014

(65) Prior Publication Data
US 2016/0166370 A1    Jun. 16, 2016

(51) Int. Cl.
*A61F 2/01* (2006.01)

(52) U.S. Cl.
CPC ........... *A61F 2/01* (2013.01); *A61F 2002/011* (2013.01); *A61F 2002/016* (2013.01); *A61F 2230/005* (2013.01); *A61F 2230/0067* (2013.01)

(58) Field of Classification Search
CPC ............ A61B 17/22031; A61B 17/221; A61B 17/3468; A61B 17/50; A61B 2017/00358; A61B 2017/111; A61B 2017/22035; A61F 2/01; A61F 2002/011; A61F 2002/9528; A61F 2/013; A61M 25/0119
USPC .......................... 606/113, 114, 127; 604/271
See application file for complete search history.

(56) References Cited

U.S. PATENT DOCUMENTS

| | | |
|---|---|---|
| 3,952,737 A | 4/1976 | Lipfert et al. |
| 4,085,743 A | 4/1978 | Yoon |
| 4,174,715 A | 11/1979 | Hasson |
| 4,467,802 A | 8/1984 | Maslanka |
| 4,611,594 A | 9/1986 | Grayhack et al. |
| 4,655,219 A | 4/1987 | Petruzzi |
| 4,723,936 A | 2/1988 | Buchbinder et al. |
| 4,873,978 A | 10/1989 | Ginsburg |
| 4,960,411 A | 10/1990 | Buchbinder |
| 5,011,488 A | 4/1991 | Ginsburg |
| 5,041,093 A | 8/1991 | Chu |
| 5,074,845 A | 12/1991 | Miraki et al. |
| 5,098,440 A | 3/1992 | Hillstead |

(Continued)

FOREIGN PATENT DOCUMENTS

| | | |
|---|---|---|
| EP | 1172073 A1 | 1/2002 |
| JP | H 10-509623 A | 9/1998 |

(Continued)

OTHER PUBLICATIONS

WO, PCT/US2014/042343 ISR and Written Opinion, dated Sep. 30, 2014.

(Continued)

*Primary Examiner* — Katrina M Stransky
*Assistant Examiner* — Lindsey Bachman
(74) *Attorney, Agent, or Firm* — One LLP

(57) ABSTRACT

Funnel-trap type devices or systems made of braid are described for capture and retrieval or, instead, capture and subsequent release of Inferior Vena Cava (IVC) filters or other medical devices. Delivery and/or retrieval devices, kits in which they are included, methods of use and methods of manufacture are all contemplated.

17 Claims, 4 Drawing Sheets

(56) References Cited

U.S. PATENT DOCUMENTS

| | | | |
|---|---|---|---|
| 5,102,415 A | 4/1992 | Guenther et al. | |
| 5,549,626 A | 8/1996 | Miller et al. | |
| 5,601,595 A | 2/1997 | Smith | |
| 5,653,684 A | 8/1997 | Laptewicz et al. | |
| 5,662,671 A | 9/1997 | Barbut et al. | |
| 5,746,251 A | 5/1998 | Bullard | |
| 5,782,747 A | 7/1998 | Zimmon | |
| 5,800,457 A | 9/1998 | Gelbfish | |
| 5,814,064 A | 9/1998 | Daniel et al. | |
| 5,827,324 A | 10/1998 | Cassell et al. | |
| 5,846,251 A | 12/1998 | Hart | |
| 5,908,435 A | 6/1999 | Samuels | |
| 5,911,734 A | 6/1999 | Tsugita et al. | |
| 5,944,728 A | 8/1999 | Bates | |
| 6,001,118 A | 12/1999 | Daniel et al. | |
| 6,156,055 A | 12/2000 | Ravenscroft | |
| 6,159,230 A | 12/2000 | Samuels | |
| 6,203,561 B1 | 2/2001 | Ramee et al. | |
| 6,210,370 B1* | 4/2001 | Chi-Sing | A61B 17/22032 604/104 |
| 6,238,412 B1 | 5/2001 | Dubrul et al. | |
| 6,251,092 B1 | 6/2001 | Qin et al. | |
| 6,251,122 B1 | 6/2001 | Tsukernik | |
| 6,264,671 B1 | 7/2001 | Stack et al. | |
| 6,273,900 B1 | 8/2001 | Nott et al. | |
| 6,290,710 B1 | 9/2001 | Cryer et al. | |
| 6,306,163 B1 | 10/2001 | Fitz | |
| 6,336,934 B1 | 1/2002 | Gilson et al. | |
| 6,395,017 B1 | 5/2002 | Dwyer et al. | |
| 6,443,972 B1 | 9/2002 | Bosma et al. | |
| 6,447,531 B1 | 9/2002 | Amplatz | |
| 6,458,151 B1 | 10/2002 | Saltiel | |
| 6,485,501 B1 | 11/2002 | Green | |
| 6,500,182 B2 | 12/2002 | Foster | |
| 6,569,184 B2 | 5/2003 | Huter | |
| 6,602,271 B2 | 8/2003 | Adams et al. | |
| 6,605,102 B1 | 8/2003 | Mazzocchi et al. | |
| 6,632,236 B2 | 10/2003 | Hogendijk | |
| 6,645,222 B1 | 11/2003 | Parodi et al. | |
| 6,663,652 B2 | 12/2003 | Daniel et al. | |
| 6,679,893 B1 | 1/2004 | Tran | |
| 6,695,813 B1 | 2/2004 | Boyle et al. | |
| 6,699,260 B2 | 3/2004 | Dubrul et al. | |
| 6,702,834 B1 | 3/2004 | Bpylan et al. | |
| 6,743,247 B1 | 6/2004 | Levinson et al. | |
| 6,780,196 B2 | 8/2004 | Chin et al. | |
| 6,800,080 B1 | 10/2004 | Bates | |
| 6,833,002 B2 | 12/2004 | Stack et al. | |
| 6,896,690 B1 | 5/2005 | Lambrecht et al. | |
| 6,958,074 B2 | 10/2005 | Russell | |
| 7,211,089 B2 | 5/2007 | Kear et al. | |
| 7,322,989 B2 | 1/2008 | Teague et al. | |
| 7,338,512 B2 | 3/2008 | McGuckin, Jr. et al. | |
| 7,377,925 B2 | 5/2008 | Poll | |
| 7,491,210 B2 | 2/2009 | Dubrul et al. | |
| 7,625,390 B2 | 12/2009 | Hendriksen et al. | |
| 7,658,747 B2 | 2/2010 | Forde et al. | |
| 7,731,723 B2 | 6/2010 | Kear et al. | |
| 7,780,693 B2 | 8/2010 | Brady et al. | |
| 7,780,694 B2 | 8/2010 | Palmer et al. | |
| 7,837,702 B2 | 11/2010 | Bates | |
| 7,993,362 B2 | 8/2011 | Lowe et al. | |
| 8,038,704 B2 | 10/2011 | Sherburne | |
| 8,043,322 B2 | 10/2011 | Hendriksen et al. | |
| 8,163,004 B2 | 4/2012 | Amplatz et al. | |
| 8,202,309 B2 | 6/2012 | Styrc | |
| 8,273,073 B2 | 9/2012 | Levine et al. | |
| 8,298,244 B2 | 10/2012 | Garcia et al. | |
| 8,469,969 B2 | 6/2013 | Kear et al. | |
| 8,469,970 B2 | 6/2013 | Diamant | |
| 8,475,488 B2 | 7/2013 | Cartier et al. | |
| 8,512,401 B2 | 8/2013 | Murray, III et al. | |
| 8,747,597 B2 | 6/2014 | Rosqueta et al. | |
| 2001/0044595 A1 | 11/2001 | Reydel et al. | |
| 2002/0010476 A1 | 1/2002 | Mulholland et al. | |
| 2002/0062135 A1 | 5/2002 | Mazzocchi et al. | |
| 2002/0068967 A1 | 6/2002 | Drasler et al. | |
| 2002/0169474 A1 | 11/2002 | Kusleika et al. | |
| 2003/0130680 A1 | 7/2003 | Russell | |
| 2003/0176884 A1 | 9/2003 | Berrada et al. | |
| 2003/0187474 A1 | 10/2003 | Keegan et al. | |
| 2004/0049226 A1 | 3/2004 | Keegan et al. | |
| 2004/0093012 A1 | 5/2004 | Cully et al. | |
| 2004/0138677 A1 | 7/2004 | Little et al. | |
| 2004/0153118 A1 | 8/2004 | Clubb et al. | |
| 2004/0181237 A1* | 9/2004 | Forde | A61B 17/12122 606/108 |
| 2004/0199202 A1 | 10/2004 | Dubrul et al. | |
| 2005/0159770 A1 | 7/2005 | Divani et al. | |
| 2005/0182439 A1 | 8/2005 | Lowe | |
| 2005/0187570 A1 | 8/2005 | Nguyen et al. | |
| 2005/0234502 A1 | 10/2005 | Gilson et al. | |
| 2005/0267515 A1 | 12/2005 | Oliva et al. | |
| 2006/0020256 A1 | 1/2006 | Bell et al. | |
| 2006/0074446 A1 | 4/2006 | Gilson et al. | |
| 2006/0247572 A1* | 11/2006 | McCartney | A61B 8/0841 604/19 |
| 2007/0005101 A1 | 1/2007 | Fahey et al. | |
| 2007/0112374 A1 | 5/2007 | Paul et al. | |
| 2007/0149996 A1 | 6/2007 | Coughlin | |
| 2007/0173884 A1 | 7/2007 | Gilson et al. | |
| 2007/0186933 A1 | 8/2007 | Domingo et al. | |
| 2007/0244504 A1 | 10/2007 | Keegan et al. | |
| 2007/0282369 A1 | 12/2007 | Gilson et al. | |
| 2008/0091223 A1 | 4/2008 | Pokorney et al. | |
| 2008/0269774 A1 | 10/2008 | Garcia et al. | |
| 2009/0182370 A1 | 7/2009 | Volobuyev et al. | |
| 2009/0192485 A1 | 7/2009 | Heuser | |
| 2009/0198315 A1 | 8/2009 | Boudjemline | |
| 2009/0222035 A1 | 9/2009 | Schneiderman | |
| 2009/0222076 A1 | 9/2009 | Figulla et al. | |
| 2009/0248060 A1 | 10/2009 | Schneider et al. | |
| 2009/0287291 A1 | 11/2009 | Becking et al. | |
| 2010/0137846 A1 | 6/2010 | Desai et al. | |
| 2010/0256669 A1 | 10/2010 | Harris et al. | |
| 2010/0312268 A1 | 12/2010 | Belson | |
| 2010/0331949 A1 | 12/2010 | Habib | |
| 2011/0040321 A1* | 2/2011 | Cartier | A61B 17/221 606/200 |
| 2011/0046611 A1 | 2/2011 | Christiansen | |
| 2011/0125180 A1 | 5/2011 | Tripp et al. | |
| 2011/0178547 A1 | 7/2011 | Paul, Jr. et al. | |
| 2011/0282274 A1 | 11/2011 | Fulton, III | |
| 2011/0288572 A1 | 11/2011 | Martin | |
| 2011/0307002 A1 | 12/2011 | Gilson et al. | |
| 2012/0041473 A1 | 2/2012 | Nigon | |
| 2013/0184738 A1 | 7/2013 | Laroya et al. | |
| 2013/0197567 A1 | 8/2013 | Brady et al. | |
| 2013/0267848 A1 | 10/2013 | Fearmot et al. | |
| 2013/0289694 A1 | 10/2013 | Sherburne | |
| 2014/0005712 A1 | 1/2014 | Martin | |
| 2014/0024887 A1 | 1/2014 | Ishii et al. | |
| 2014/0155930 A1 | 6/2014 | Bennett et al. | |
| 2014/0277089 A1 | 9/2014 | Goode et al. | |
| 2014/0373334 A1 | 12/2014 | Gamarra et al. | |
| 2015/0105819 A1 | 4/2015 | Becking et al. | |
| 2015/0366650 A1 | 12/2015 | Zi et al. | |
| 2016/0296315 A1 | 10/2016 | Yachia et al. | |

FOREIGN PATENT DOCUMENTS

| | | |
|---|---|---|
| JP | 2003-501203 A | 1/2003 |
| JP | 2004-524049 A | 8/2004 |
| JP | 2005-523767 A | 8/2005 |
| JP | 2007-508902 A | 4/2007 |
| JP | 2008-513121 A | 5/2008 |
| JP | 2008-514276 A | 5/2008 |
| JP | 4109422 B2 | 7/2008 |
| JP | 2009-517124 A | 4/2009 |
| JP | 4320142 B2 | 8/2009 |
| JP | 2013-154183 A | 8/2013 |

(56) References Cited

FOREIGN PATENT DOCUMENTS

KR          101133157 B1     4/2012
WO        WO 00/16846 A1     3/2000

OTHER PUBLICATIONS

WO, PCT/US2015/058898 ISR and Written Opinion, dated Feb. 11, 2016.
WO, PCT/US2015/065074 ISR and Written Opinon, dated Mar. 22, 2016.
WO, PCT/US2015/065025 ISR and Written Opinon, dated Apr. 1, 2016.
WO, PCT/US2015/065102 ISR and Written Opinon, dated Sep. 8, 2016.
EP, 14810753.2 Extended Search Report, dated Nov. 24, 2016.
EP, 15867928.2 Supplementary Search Report, dated Jun. 5, 2018.
EP, 15867562.9 Supplementary Search Report, dated Jun. 5, 2018.
JP, 2016-519686 Official Action, dated Mar. 28, 2018.
EP, 14907807.3 Supplementary Search Report, dated May 15, 2018.

\* cited by examiner

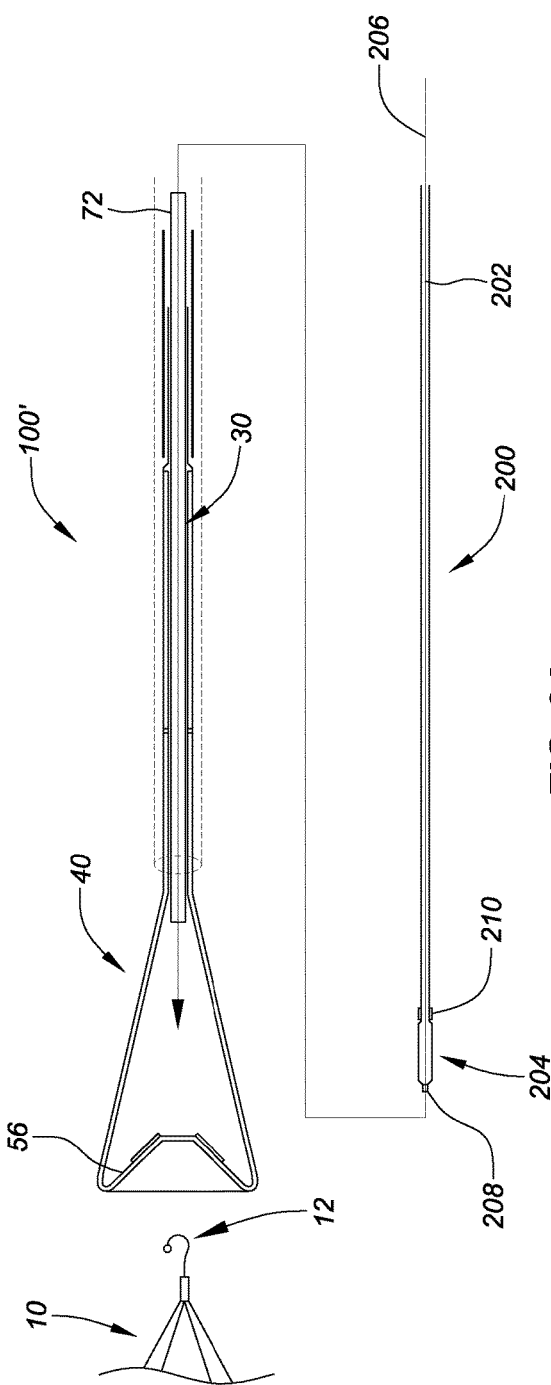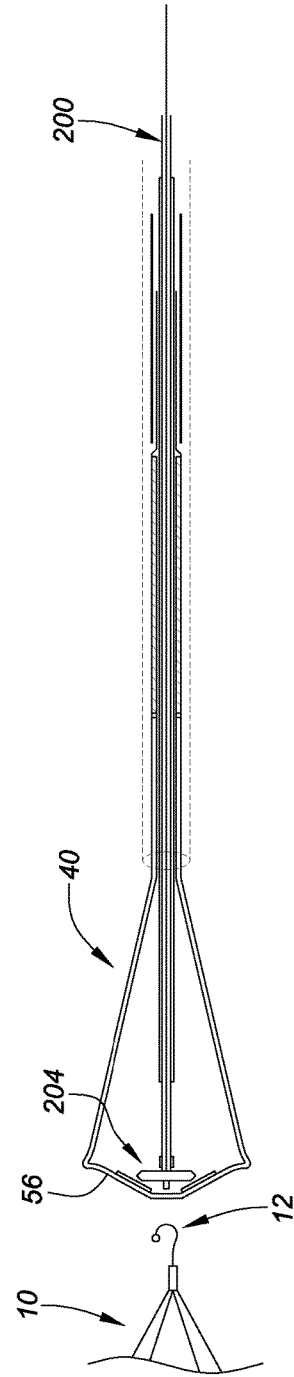

IVC FILTER RETRIEVAL SYSTEMS WITH RELEASABLE CAPTURE FEATURE

FIELD

The embodiments described herein relate to endovascular temporary Inferior Vena Cava (IVC) filter or other implant retrieval devices or system and methods.

BACKGROUND

Temporary IVC filters are placed much like permanent filters, but are designed so that they may be retrieved in a separate endovascular procedure, generally from a femoral vein or an internal jugular vein approach. Most of the currently available temporary filters include a hook-like feature with which they can be captured and received within a catheter or sheath for removal by employing a gooseneck snare or a multi-loop snare.

While retrieval is a simple procedure in principle, difficulty is often encountered capturing a filter's hook with the snare loop(s). Such difficulty is compounded when the filter is tilted or off-kilter in placement. Several filters are designed to avoid such orientation. However, the problem remains common because the device is not anchored into the IVC in a stable fashion. Constant blood flow in addition to blood clots can disorient the filter within the IVC making recapture difficult. Accordingly, there remains a need for filter improved retrieval systems.

SUMMARY

The example embodiments described herein meet this and/or other needs, particularly with respect to addressing any complications experience during filter retrieval. Specifically, the subject devices or systems include feature(s) that allow for capture or retrieval and subsequent release of Inferior Vena Cava (IVC) filters or other medical devices if desired. In other words, the subject devices allow for reversal of IVC filter capture once it is achieved in case so-called "bail-out" is desired in order to avoid other complications.

The ability to release a captured or hooked IVC filter may be desirable in cases where the amount of tissue ingrowth with the filter is greater than expected. Other reasons for wanting to (in a sense) reverse course during a filter retrieval procedure may by expressed by physicians with skill in the art.

In the subject systems, the reversal option is both figurative and literal with respect to the operation of the design. Namely, features are provided for reconfiguring and reversing the orientation of a flap incorporated in the retrieval device that is otherwise intended to capture the IVC filter. In an inverted state, the flap in the retrieval device is configured to retain the filter. When the flap is everted (i.e., turned outward or inside out) it either releases or allows release of the filter.

In one embodiment, a pusher wire is incorporated in the design to facilitate everting an otherwise inverted flap configuration. This wire may comprise a pair of filaments in side-by-side configuration, a pair (or more) of filaments twisted and set to form a wire cable, part of a catheter construction, or be otherwise configured.

In another embodiment, a separate plunger or pusher element may be deployed through a lumen (optionally a central lumen) of the retrieval device and then be expanded and advanced further to effect flap eversion. In this example, the plunger device may be provided separately and tracked through a lumen in the retrieval device when desired for use. Alternatively, the plunger may be incorporated or housed in the retrieval device as in a kit or combination.

However configured, the subject retrieval devices or systems, kits in which they are included (with and without assembly), methods of use and manufacture (including assembly of the constituent components in vivo or ex vivo) are all included within the scope of the present disclosure. Some aspects of the same are described above, more detailed discussion is presented in connection with the figures below.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 3A and 3B are side-sectional views depicting another example embodiment of a retrieval system including a plunger for filter capture feature reversal.

DETAILED DESCRIPTION

Before the present subject matter is described in detail, it is to be understood that this disclosure is not limited to the particular example embodiments described, as such may, of course, vary. It is also to be understood that the terminology used herein is for the purpose of describing particular embodiments only, and is not intended to be limiting, since the scope of the present disclosure will be limited only by the appended claims.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

Figure 1A:
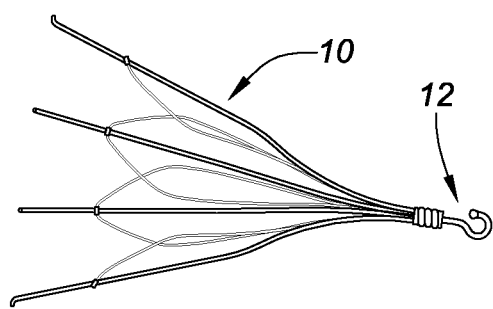
FIGS. 1A and 1B are photographs of example embodiments of IVC filter variations as may be used in the present system.
Figure 1B:
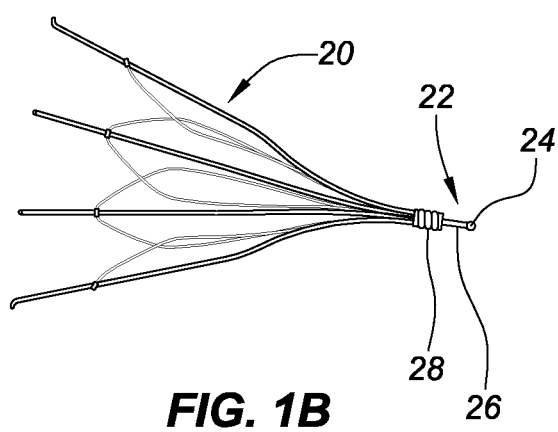

FIG. 1A shows a GÜNTHER TULIP (Cook Medical, Inc.) temporary IVC filter 10 with a hook 12 end interface for retrieval. As shown in FIG. 1B for an IVC filter 20, the hook may be modified or substituted for a nubbin-type interface 22. The nubbin 24 may comprise a laser-formed or solder-formed protuberance or bump on an extension 26 from a hub 28. Alternatively, a/the filter retrieval interface 22 may comprise a band (e.g., a Pt marker band) mounted (e.g., by swaging, welding, gluing, etc.) on a/the extension 26. However the enlargement is created, its interaction with the rest of the system for capture and/or release will be apparent in the following figures.

Figure 2A:
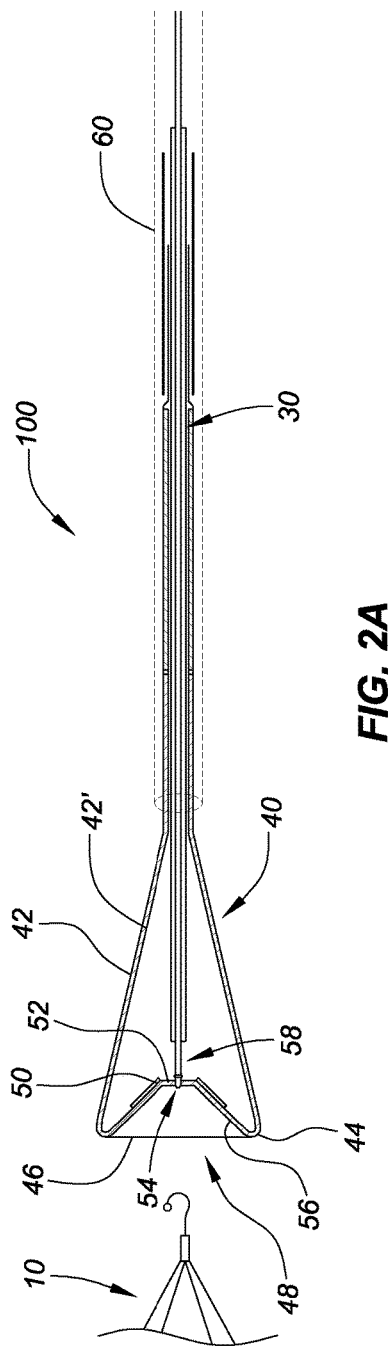
FIGS. 2A-2C are side-sectional views depicting an example embodiment of a first retrieval system including reversible filter capture features.

FIG. 2A provides a cross-sectional view of a distal end of a retrieval system 100 that is adapted to release or reversibly capture a medical device (such as filter 10 or 20). System 100 includes a shaft 30 with a distal extension 40 in the form of a funnel-trap structure made of braid material. In use with a patient's vasculature, the shaft is received within an elongate sleeve 60 (that may be a commercially available catheter or a custom part of the overall system 100).

In the various system architectures, the catheter or pusher shaft and/or sleeve 30 (and that of the plunger detailed further below) may include a simple extrusion (e.g., PTFE, FEP, PEEK, PI, etc.) or may be constructed using conventional catheter construction techniques and include a liner, braid support and outer jacket, metal hypotube, etc. The frame of filter 10 or 20 may be constructed using conventional laser cutting and electropolishing techniques and/or be otherwise constructed. In embodiments intended for tracking through a guide/delivery catheter without an incorporated sheath, a loading sheath may be employed. Advantageously, any such loading sheath is splittable. Other typical percutaneous access instruments (such as wires, etc.), valves and other hardware may also be employed in connection with the embodiments.

The funnel-trap structure 40 may be made as a subassembly and attached to the catheter/pusher shaft. International Patent Application No. PCT/US14/42343 and U.S. patent application Ser. No. 14/569,500, each of which are incorporated by reference herein in their entirety for all purposes, detail optional steps in the manufacture of a pre-form for constructing the funnel-trap portion of the final device. In general, the aforementioned forming methods are ones in which a heatset (possibly multiple-staged heatset) preform is provided that is substantially cylindrical in shape and includes an interior folded "flap" section. As such, the preform resembles the subject device in its fully compressed state for catheter tracking. Then, the preform is expanded (e.g., in a conical shape) to a desired "working" diameter and heatset accordingly. It may be heatset into a conical shape and be ready for mounting, or it may be heatset in a conical shape and transformed to a conical shape by mounting to catheter body 30.

The braid from which the retrieval system extension 40 is optionally made may comprise Nitinol (preferably that is superelastic at body temperature), CoCr, Stainless Steel or another biocompatible material. The braid advantageously incorporates between 72 and 288 (more typically between 96 or 144 and 192) filament "ends" in a 1-over-1, a 2-over-2 or other maypole braided pattern. With (superelastic) Nitinol, the wire is advantageously between about 0.001 and about 0.003 inches in diameter. In which case, a supple and relatively "smooth" matrix surface is provided from which to construct the flexible funnel-trap architecture shown and described. The value of such a surface is in its atraumatic aspect and/or ability to help guide in IVC filter interface into position for capture even if it is oriented off-angle. To further assist with recapture, the funnel trap structure may be selectably directable.

The braid may include so-called "axial" filaments as well. These may be used to improve column strength in a finally-formed device. The axial filaments may be incorporated in a/the maypole braided pattern when it is being formed or be added later manually. Alternatively, (and as shown in FIG. 2A) the funnel trap structure 40 may include interposed support member(s) # as further described in U.S. Provisional Patent Application Ser. No. 62/091,433, which is incorporated by reference herein in its entirety for all purposes.

The so-called "funnel trap" structure or extension 40 may be generally frusto-conical in shape as shown or otherwise configured. With an outer conical shape (i.e., triangular shape in cross section) the structure is highly supportive for any necessary or desirable tissue discretion that might need to occur to free an emplaced filter. Still, the device may be bowed outward along its sides or otherwise configured.

FIG. 2A, illustrates further constructional options and details. Here, inner and outer braid layers 42/42' are heatset using conventional techniques (e.g., in a furnace, salt pot, etc.) in a funnel shape with distal bends 44 in the braid wire forming an outer rim 46 with a large(r) distal opening 48 and meeting at inner bends 50 forming an inner opening or rim 52 with a small(er) more proximal opening 54. Stated otherwise, the braid used to construct the funnel-shape trap is folded back (e.g., in a flap 56) at the distal opening to provide a more proximal opening.

Importantly, the distal rim opening 48 is larger than the more proximal rim opening 54 to operate in guiding filter engagement feature(s) or enlargement 12/24 into a pocket 58 proximal to and/or radially adjacent flap 56 where it is captured and subsequently locked upon advancing sleeve 60. Initial capture of filter 10 in this manner is shown in FIG. 2B.

To help ensure capture, the sleeve 60 may be advanced fully over trap section 40 before withdrawal into a separate catheter. In other words, advancing sleeve 60 (be it a system or device-integral sleeve or in situ catheter) over funnel section 40 "closes the trap" and securely captures the implant to be retrieved. Otherwise, shaft 30 may be withdrawn until the implant is pulled into the access catheter originally used to introduce system 100. Any or all such activity may be visualized fluoroscopically by a physician by way of marker features incorporated in system 100.

Notably, system 100 may be used identically when capturing a filter 20 with a more nub or nubbin 24 end interface. In which case, the capture reversal features detailed below may not need to be used to release the implant end. However, by so-including the features, a solution is provided to handle a wider array of filters and any need for release of capture, once achieved.

Figure 2B:
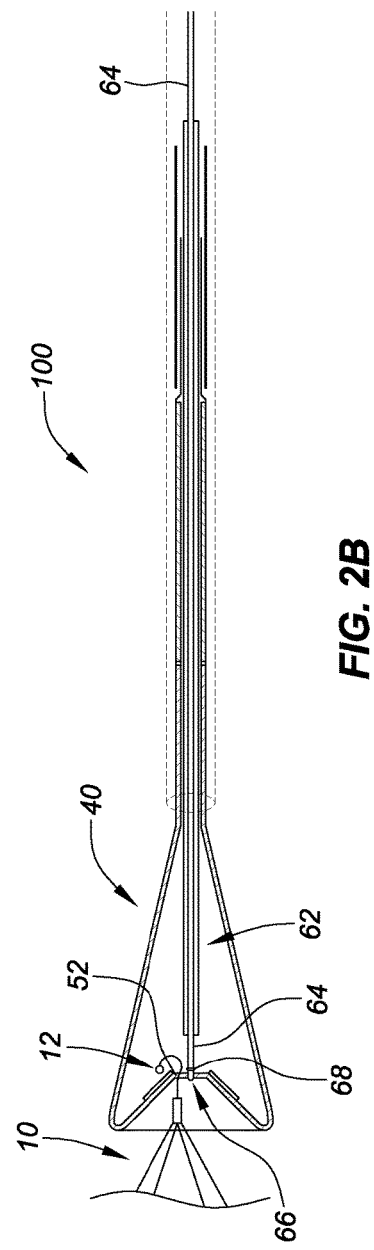
Figure 2C:
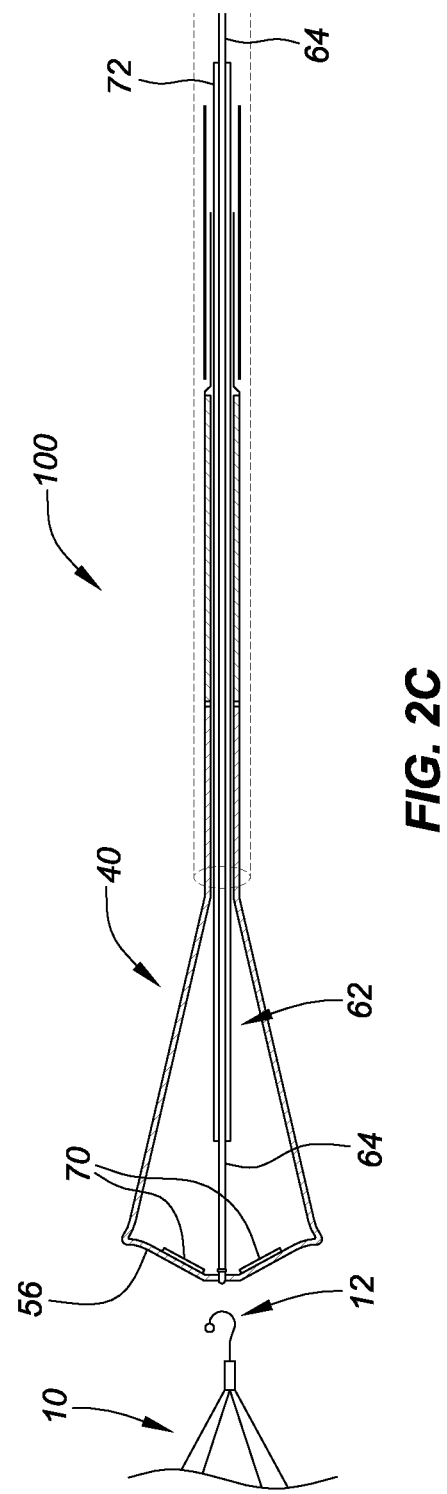

Regarding the subject capture release or reversal features, in the embodiment shown in FIGS. 2A-2C, these are provided in connection with inner shaft 62 and push "wire" 64. In the configuration shown (and fully labeled with callouts in FIG. 2B), wire filaments are looped over or through a section of rim 52 forming a "U" shape 66 secured by a band 68 (such as a crimped PT marker band). Secured to the braid as such, when wire 64 is advances as shown in FIG. 2C, the flap section 56 of extension 40 can be moved from an inverted configuration to an everted configuration. This frees hook 12 of the filter 10.

The action for expelling or releasing hook 12 is clearly apparent. It may be accompanied with withdrawing shaft 30 so that the hook can slip out of the reversed flap. Moreover, flap 56 may incorporate a coating 70 (e.g., TICOFLEX urethane coating) on its inner surface in order to secure the braid against entanglement or entrapment of the hook if pulled into the flap when the device is in the configuration shown in FIG. 2B.

The system 100' in FIGS. 3A and 3B is similar to the above except that a more complex pusher 200 is substituted for pusher wire(s) 64. This pusher 200 may be received within lumen 72 of catheter body 30 (as was wire 64).

Pusher 200 may be regarded or referred to as a "plunger" given its function as seen the figures. Namely, pusher 200 is advanced within lumen 72 after its expansion within the funnel trap extension 30 of the system and used to push flap 56 outward to effect implant engagement feature release. The pusher may reside in lumen 72 during introduction of system 100' during a medical procedure. Alternatively, it may be packages separately and inserted and tracked through lumen 72 "on-demand" if a physician decides that release of a captured implant 10 is somehow desirable.

In any case, pusher 200 comprises a sleeve 202 and an expandable distal section 204. The expandable distal section may comprise braid as shown. A pull wire 206 for braid actuation from pushed-out and compressed, to pulled-in an expanded may be included within the sleeve. Otherwise, the braid (or other material such as tube-cut Nitinol stent architecture) may be heatset in the enlarged configuration to self-expand once exiting lumen and connected to a distal end.

In the variation shown in FIGS. 3A and 3B (i.e., with the braid-based section 204) the distal ends of the braid may be secured to wire 206 within a distal Pt marker band 208. Another marker band 210 may be provided at a proximal end of the expandable section securing the proximal ends of the braid to braid ends to sleeve or shaft 202. As such, when pull wire 206 is actuated, the expansion and/or contraction of section 204 can be detected (i.e., by viewing actuation of the markers) even if it the material of the expandable section is not itself fluoroscopically visible.

VARIATIONS

The subject methods, including methods of use and/or manufacture, may be carried out in any order of the events which is logically possible, as well as any recited order of events. Medical methods may include any of a hospital staffs activities associated with device provision, implant positioning, re-positioning, retrieval and/or release.

Furthermore, where a range of values is provided, it is understood that every intervening value, between the upper and lower limit of that range and any other stated or intervening value in the stated range is encompassed within the disclosure. Also, it is contemplated that any optional feature of the embodiments described may be set forth and claimed independently, or in combination with any one or more of the features described herein.

Reference to a singular item includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the scope of the claims by features, functions, steps, or elements that are not within that scope.

The invention claimed is:

1. A medical method performed in the vasculature of a patient, the method comprising:
   advancing a funnel-trap shaped retrieval extension of a retrieval device over a proximal end of an implanted medical device, wherein the retrieval extension comprises braid with a first fold that forms two layers of the braid and a second fold in the two layers of the braid that forms a distal opening and an inwardly-directed flap, wherein a proximal opening is formed by the first fold;
   capturing the proximal end of the medical device with the inwardly-directed flap of the retrieval extension after the proximal end of the medical device has been advanced beyond the discrete proximal opening; and
   everting the flap to release the hooked end after capture.

2. The method of claim 1, wherein the everting is by advancing a wire connected to the inwardly-directed flap and received within a lumen of the retrieval device.

3. The method of claim 1, where the everting is by advancing a plunger including an expandable section received within the lumen of the retrieval device.

4. The method of claim 3, further comprising expanding the expandable section and pushing out the inwardly-directed flap.

5. The method of claim 3, further comprising inserting the plunger into the lumen of the retrieval device while the funnel-trap shaped retrieval extension is in the vasculature of the patient.

6. The method of claim 1, further comprising providing a plunger with an expandable member included in the retrieval device prior to introduction into the vasculature of the patient.

7. The method of claim 1, wherein the everting is accomplished by withdrawing the retrieval device.

8. The method of claim 1, wherein the proximal end of the medical device comprises a nub or nubbin.

9. The method of claim 1, wherein the proximal end of the medical device comprises a hook.

10. The method of claim 9, further comprising capturing the hook with the inwardly-directed flap of the retrieval extension by advancing the hook beyond the discrete proximal opening such that the hook passes over the inwardly-directed flap and the discrete proximal opening.

11. A medical method performed in the vasculature of a patient, the method comprising:
   advancing a funnel-trap shaped retrieval extension of a retrieval device over a hooked end of an implanted medical device, wherein the retrieval extension comprises braid with a first fold that forms two layers of the braid and a second fold in the two layers of the braid that forms a distal opening and an inwardly-directed flap, wherein a proximal opening is formed by the first fold;

capturing the hooked end of the medical device with the inwardly-directed flap of the retrieval extension by advancing the hooked end of the medical device beyond the proximal opening such that the hooked end of the medical device passes over the inwardly-directed flap; and everting the flap to release the hooked end after capture.

12. The method of claim 11, wherein the everting is by advancing a wire connected to the inwardly-directed flap and received within a lumen of the retrieval device.

13. The method of claim 11, where the everting is by advancing a plunger including an expandable section received within the lumen of the retrieval device.

14. The method of claim 13, further comprising expanding the expandable section and pushing out the inwardly-directed flap.

15. The method of claim 13, further comprising inserting the plunger into the lumen of the retrieval device while the funnel-trap shaped retrieval extension is in the vasculature of the patient.

16. The method of claim 11, further comprising providing a plunger with an expandable member included in the retrieval device prior to introduction into the vasculature of the patient.

17. The method of claim 11, wherein the everting is accomplished by withdrawing the retrieval device.

\* \* \* \* \*